United States Patent
Merlin et al.

(10) Patent No.: US 11,865,349 B2
(45) Date of Patent: Jan. 9, 2024

(54) DISPLAY DEVICE FOR A PROGRAMMING APPARATUS

(71) Applicant: BIOTRONIK SE & Co. KG, Berlin (DE)

(72) Inventors: Julian Merlin, Berlin (DE); Klaus Brandau, Eichwalde (DE); Christoph Hammerschmidt, Berlin (DE); Andreas Fechner, Berlin (DE); Enrico Kurecki, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 285 days.

(21) Appl. No.: 17/255,681

(22) PCT Filed: Jun. 19, 2019

(86) PCT No.: PCT/EP2019/066230
§ 371 (c)(1),
(2) Date: Dec. 23, 2020

(87) PCT Pub. No.: WO2020/002097
PCT Pub. Date: Jan. 2, 2020

(65) Prior Publication Data
US 2021/0283407 A1  Sep. 16, 2021

(30) Foreign Application Priority Data
Jun. 29, 2018 (DE) .................... 10 2018 210 760.2

(51) Int. Cl.
*A61N 1/372* (2006.01)
*G06F 3/041* (2006.01)
*G06F 3/044* (2006.01)

(52) U.S. Cl.
CPC ..... *A61N 1/37247* (2013.01); *A61N 1/37229* (2013.01); *G06F 3/044* (2013.01); *G06F 3/0412* (2013.01)

(58) Field of Classification Search
CPC ............ A61N 1/37247; A61N 1/37229; G06F 3/0412; G06F 3/044
See application file for complete search history.

(56) References Cited

U.S. PATENT DOCUMENTS

2005/0075686 A1  4/2005 Phillips et al.
2011/0141055 A1  6/2011 Hsu
(Continued)

FOREIGN PATENT DOCUMENTS

DE  102012216821 A1  3/2013

OTHER PUBLICATIONS

International Search Report (PCT/ISA/210) and translation and Written Opinion (PCT/ISA/237) dated Jan. 7, 2020, by the European Patent Office as the International Searching Authority for International Application No. PCT/EP2019/066230.
(Continued)

*Primary Examiner* — Peter D McLoone
(74) *Attorney, Agent, or Firm* — Buchanan Ingersoll & Rooney PC

(57) ABSTRACT

The disclosure relates to a display device for a programmer of an implant, wherein the display device comprises a frame which receives and holds the following components: a display module which is designed to generate and display a representation, a shielding layer which is arranged on the display module, a flat capacitive touch sensor which is arranged on the shielding layer, and a cover which is arranged on the touch sensor. The display device further comprises an antenna, wherein the antenna is designed to
(Continued)

transmit and/or receive in the MICS frequency band. Furthermore, a programmer for an implant is disclosed.

6 Claims, 3 Drawing Sheets

(56) References Cited

U.S. PATENT DOCUMENTS

| | | | |
|---|---|---|---|
| 2012/0307348 A1* | 12/2012 | Nomura | G02F 1/172 |
| | | | 359/296 |
| 2013/0077227 A1 | 3/2013 | Chen et al. | |
| 2013/0135258 A1 | 5/2013 | King et al. | |
| 2016/0199659 A1* | 7/2016 | Jiang | A61N 1/37247 |
| | | | 607/60 |
| 2020/0044482 A1* | 2/2020 | Partovi | H02J 50/80 |

OTHER PUBLICATIONS

Parker Hannifin Corporation, "EMI Shielded PCAP and REsistive Touchscreens", May 31, 2016, https://www.parker.com/Literature/Chomerics/Parker%20Chomerics%20CHO-TOUCH%20EMI%20TOUCHSCREENS%20TB1116.pdf, retrieved on Oct. 1, 2019, 4 pages, XP002794687.

* cited by examiner

DISPLAY DEVICE FOR A PROGRAMMING APPARATUS

CROSS-REFERENCE TO RELATED APPLICATIONS

This application is the United States national phase under 35 U.S.C. § 371 of PCT International Patent Application No. PCT/EP2019/066230, filed on Jun. 19, 2019, which claims the benefit of German Patent Application No. 10 2018 210 760.2, filed on Jun. 29, 2018, the disclosures of which are hereby incorporated by reference herein in their entireties.

TECHNICAL FIELD

The present disclosure relates to a display device for a programmer or programming apparatus of an implant.

BACKGROUND

Some medical implants, such as pacemakers, may communicate with a programmer to set implant parameters and/or to transfer data from the implant to the programmer. For a user, simple operation of the programmer is desirable.

Programmers with resistive touch sensors (touchscreens) are known. However, a resistive touch sensor only allows the detection of a single touch, which limits the operating possibilities.

The present disclosure is directed toward overcoming one or more of the above-mentioned problems, though not necessarily limited to embodiments that do.

SUMMARY

It is an object of the present invention to specify improved technologies for an implant programmer or programming apparatus, the two of which are used interchangeably herein. In particular, the handling of the programmer should be improved.

According to one aspect, a display device for a programmer of an implant is provided. The display device comprises a frame which receives and holds the following components: a display module designed to generate and display a representation, a shielding layer arranged on the display module, a flat capacitive touch sensor arranged on the shielding layer, and a cover arranged on the touch sensor. The display device also has an antenna. The antenna is designed to transmit and/or receive in the MICS frequency band.

According to another aspect, a programmer for an implant with a display device is disclosed, and the display device may have the features disclosed here.

The MICS frequency band (MICS—medical implant communication service) covers the frequencies from 401 MHz to 406 MHz. A core range of the MICS frequency band covers the frequencies from 402 MHz to 405 MHz. A first sideband of the MICS frequency band covers the frequencies from 401 MHz to 402 MHz. A second sideband of the MICS frequency band covers the frequencies from 405 MHz to 406 MHz. The MICS frequency band is used for radio communication with medical implants. It is divided into 25 kHz channels, with one implant using up to 300 kHz. Data rates up to 800 kbit/s are possible.

The implant can be an ultra low power active medical implant (ULP-AMI). The MICS frequency band is particularly suitable for communication with such an implant.

In one embodiment, a system with an implant, for example an implantable pacemaker or an implantable cardioverter/defibrillator (ICD), and a programmer is thus provided. The programmer is configured to communicate wirelessly with the implant, especially in the MICS frequency band. The programmer has a capacitive touch sensor (touchscreen). This allows easy and user-friendly operation of the programmer. It is possible to detect gestures and several simultaneous touches (multi-touch).

The flat capacitive touch sensor may be a projected capacitive touch sensor (PCAP touchscreen). A PCAP touchscreen uses two layers with a conductive pattern (usually stripes or diamonds). The layers are isolated from each other. A first layer serves as a sensor; a second layer acts as a driver. If a finger is located at the intersection of two strips, the capacitance of the capacitor changes and a greater signal reaches the receiver strip. The main advantage of this system is that the sensor may be mounted on the back of a cover (the recognition is "projected through", hence the name). This means, for example, that the operation may be carried out on a glass surface that is practically free of wear and tear.

The shielding layer may be configured to shield the capacitive touch sensor and the antenna to avoid interference.

The cover may be designed as a glass panel.

The display module may be realized as an LCD screen (LCD—liquid crystal display).

The display module, the shielding layer, the touch sensor and the cover may be of the same size, in particular the same area.

The antenna may be mounted on the frame.

The frame may have a quadrangular shape, for example rectangular or square. The antenna may be placed in a corner region of the frame.

The antenna may have a curved shape, with a first antenna wing and a second antenna wing enclosing an angle, for example a right angle. The antenna may be located in the corner region of the frame such that the first antenna wing extends from the corner in one direction along the frame and the second antenna wing extends from the corner in a second direction along the frame, the first direction and the second direction being different.

The display device may have two antennas. A first antenna may be located in a first corner region of the frame and a second antenna may be located in a second corner region of the frame. For the first antenna and the second antenna, the explanations for the antenna apply analogously. In particular, the first antenna and the second antenna may each have a curved shape and may be arranged in two corner regions of the frame.

The shielding layer may comprise a grid of an electrically conductive material (for example a metal grid or a shielding foil with a metal grid) and a plastic substrate. The grid may be arranged on the plastic substrate. The plastic substrate may be made of a thermoplastic material, for example PET (PET—polyethylene terephthalate). The grid may be a photo-etched grid.

The shielding layer may have a transmission of more than 85% of visible light (wavelength from 400 nm to 750 nm) and may have a shielding of 63 dB or less at a frequency of 400 MHz.

The shielding layer may be attached to the display module with an adhesive. The adhesive may be an optically transparent adhesive. The adhesive may be electrically conductive. The adhesive may be a one-component silicone adhesive and may contain nickel graphite particles, for example.

The display device may have a control unit coupled to the touch sensor with a line, the line being provided with a filter, for example a ferrite filter. A plurality of conductors may be provided to connect the control unit to the touch sensor. Some or all of the plurality of conductors may be provided with a filer.

The control unit may be arranged on a printed circuit board. The printed circuit board may be provided with a shielding plate. The printed circuit board may be connected to a housing of the display device via an earth contact.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

In the following, exemplary embodiments will be explained with reference to the figures, in which.

DETAILED DESCRIPTION

In the following, like reference signs are used for like components.

Figure 1:
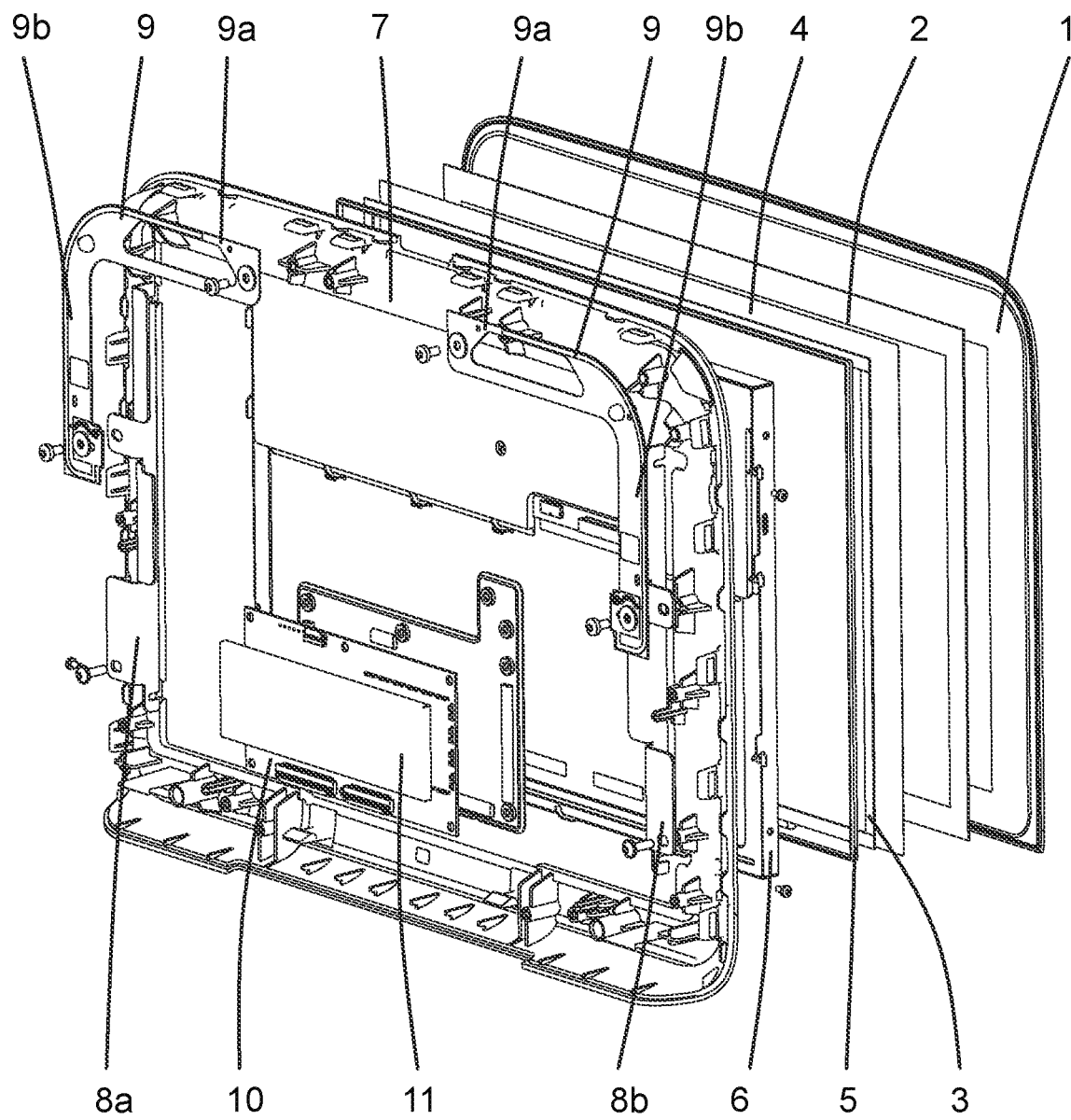
FIG. 1 shows an exploded view of a display device.

FIG. 1 shows an embodiment of a display device. A frame 7 accommodates an LCD panel 6. A shielding foil 4 is attached to the LCD panel 6 by means of an electrically conductive adhesive layer 5. A PCAP touch sensor 2 is attached to the shielding foil 4 with an adhesive 3. The arrangement is covered by a cover glass 1. The LCD panel 6 is held in the frame 7 by two holders 8a, 8b. Two antennas 9 are fixed to the frame 7. Below the LCD panel 6 there is a printed circuit board with a control unit 10, which is shielded with a shielding 11.

The two antennas 9 each have a curved shape with a first antenna wing 9a and a second antenna wing 9b. They enclose a substantially right angle. The two antennas 9 are mounted on the respective metal holders 8a and 8b, which are arranged at the corners of frame 7, so that the antenna wings 9a, 9b extend along frame 7 from the respective corners.

The antennas 9 are configured to communicate with an implant in the MICS frequency band.

The shielding foil 4 has a metal grid with a very fine grid structure and is optimised for display devices. The transmission of the shielding foil 4 is >85%. The shielding foil 4 has a good shielding effect in the MICS frequency band (approx. 63 dB or less than 400 MHz). The product Emi-Clare MicroMesh 2nd Generation may be used, for example.

For the adhesive layer 5 the adhesive "AS-RTV25" from Aerospace Sealants may be used. The adhesive is a 1-component silicone adhesive, filled with nickel-graphite particles and has a very good electrical conductivity.

Figure 2:
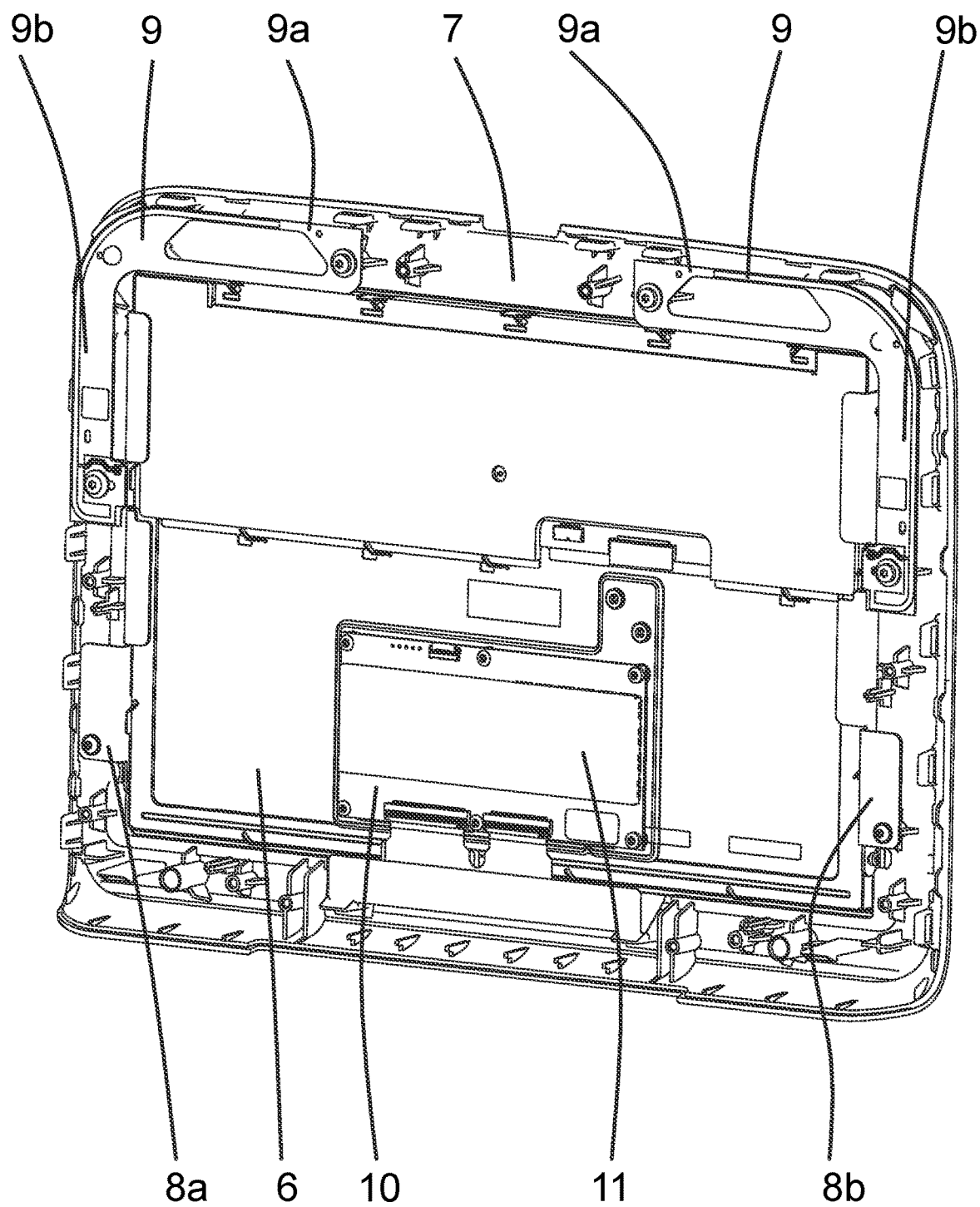
FIG. 2 shows a perspective view from behind of the display device as shown in FIG. 1.
Figure 3:
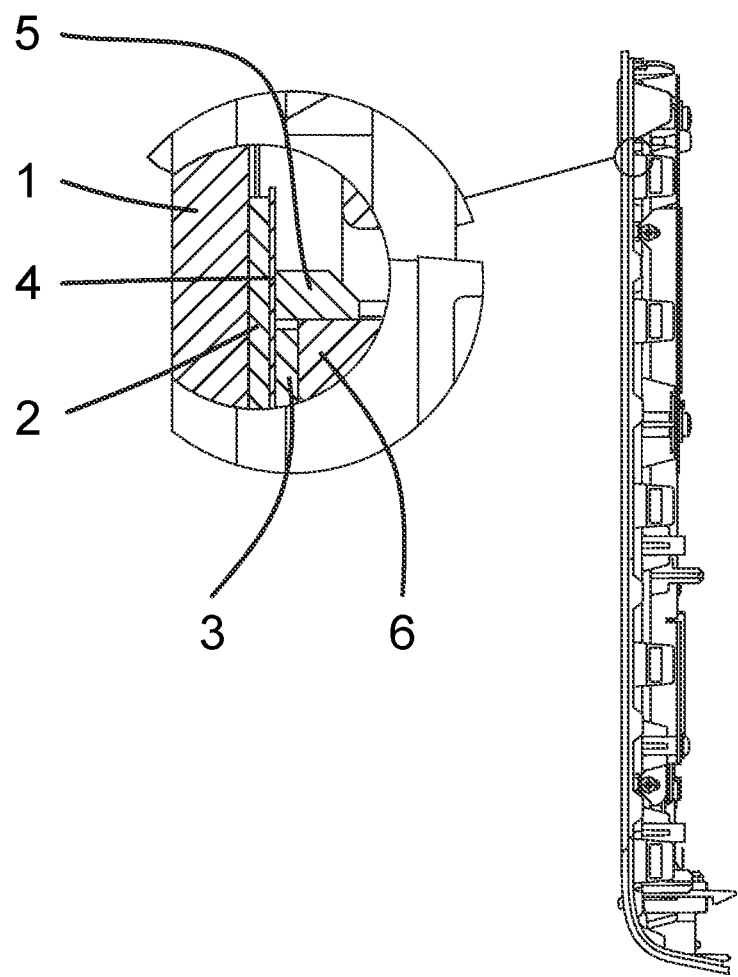
FIG. 3 shows a schematic detailed view of the display device.

FIG. 2 shows the display device in the assembled state.
FIG. 3 shows a detailed view of a portion of the display device.

The embodiments disclosed here may have the following advantages:
use of capacitive touch technology for a programmer enables multi-finger operation, and zoom and swipe techniques,
robust design of the control panel, and
sealing against detergents and disinfectants.

The features disclosed in the description, the claims and the figures may be relevant to the realisation of embodiments either individually or in any combination with each other.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

LIST OF REFERENCE SIGNS 1 cover glass
2 PCAP touch sensor
3 adhesive
4 shielding foil
5 adhesive layer
6 LCD panel
7 frame
8a, 8b holder
9 antenna
9a first antenna wing
9 second antenna wing
10 control unit
11 shielding

The invention claimed is:

1. A display device for a programmer of an implant, wherein the display device comprises a square shaped frame which receives and holds the following components:
a display module which is designed to generate and display a representation,
a shielding layer which is arranged on the display module,
a flat capacitive touch sensor, which is arranged on the shielding layer, and
a cover placed on the touch sensor,
wherein the display device further comprises two separate antennas, and wherein:
a first antenna is arranged in a first corner region of the square shaped frame and a second antenna is arranged in a second separate corner region of the square shaped frame;
each individual antenna is designed to transmit and/or receive in the MICS frequency band; and
each of the first antenna and the second antenna includes a first antenna wing and a second antenna wing arranged to enclose an angle, the first antenna wing of each antenna extends from a respective corner of the corner region in one direction along the square shaped frame and the second antenna wing of each antenna extends from the respective corner in a second direction along the square shaped frame, the first direction being different from the second direction.

2. The display device according to claim 1, wherein the shielding layer comprises a grid of an electrically conductive material and a plastic substrate, and wherein the grid is arranged on the plastic substrate.

3. The display device according to claim 1, wherein the shielding layer has a transmission of more than 85% of visible light and has a shielding of 63 dB or less at a frequency of 400 MHz.

4. The display device according to claim 1, further comprising a control unit coupled to the touch sensor with a line, wherein the line is provided with a filter.

5. A programmer with a display device according to claim 1.

6. A programmer for an implant, the programmer comprising:
- a display device comprising a frame which receives and holds the following components:
  - a display module which is designed to generate and display a representation,
  - a shielding layer which is arranged on the display module,
  - a flat capacitive touch sensor, which is arranged on the shielding layer, and
  - a cover placed on the touch sensor,
- wherein the display device further comprises an antenna, and wherein the antenna is designed to transmit and/or receive in the MICS frequency band, and
- wherein the shielding layer has a transmission of more than 85% of visible light and has a shielding of 63 dB or less at a frequency of 400 MHz.

* * * * *